(12) United States Patent
Griffiths et al.

(10) Patent No.: US 8,057,427 B2
(45) Date of Patent: Nov. 15, 2011

(54) DRUG DELIVERY SYSTEM WITH A SMALL AMOUNT OF A THERAPEUTIC AGENT

(75) Inventors: Steven M. Griffiths, Ellicott City, MD (US); Robert L. Hill, Abingdon, MD (US); Gerald L. Wannarka, Glenwood, MD (US)

(73) Assignee: Meridian Medical Technologies, Inc., Columbia, MD (US)

( * ) Notice: Subject to any disclaimer, the term of this patent is extended or adjusted under 35 U.S.C. 154(b) by 97 days.

(21) Appl. No.: 12/116,437

(22) Filed: May 7, 2008

(65) Prior Publication Data
US 2008/0281271 A1    Nov. 13, 2008

Related U.S. Application Data

(60) Provisional application No. 60/928,594, filed on May 9, 2007.

(51) Int. Cl.
*A61M 35/00* (2006.01)
*A61M 5/00* (2006.01)

(52) U.S. Cl. .............. 604/89; 604/82; 604/90; 604/92; 604/135; 604/136; 604/156; 604/157; 604/187; 604/190; 604/218; 604/232

(58) Field of Classification Search ............. 604/232, 604/92, 82, 89, 90, 135, 136, 156, 157, 187, 604/190, 218, 236; 424/400–502
See application file for complete search history.

(56) References Cited

U.S. PATENT DOCUMENTS

| | | | |
|---|---|---|---|
| 3,592,245 A * | 7/1971 | Schneller et al. | 141/25 |
| 5,330,426 A | 7/1994 | Kriesel et al. | |
| 5,411,480 A | 5/1995 | Kriesel | |
| 5,779,676 A | 7/1998 | Kriesel et al. | |
| 6,641,561 B1 * | 11/2003 | Hill et al. | 604/136 |
| 2003/0068354 A1 * | 4/2003 | Reif et al. | 424/423 |
| 2003/0105423 A1 | 6/2003 | Hughes | |
| 2004/0097874 A1 | 5/2004 | Griffiths et al. | |
| 2004/0260242 A1 | 12/2004 | Hughes et al. | |
| 2006/0034929 A1 | 2/2006 | Brubaker | |
| 2006/0129122 A1 | 6/2006 | Wyrick | |
| 2007/0256688 A1 * | 11/2007 | Schuster et al. | 128/200.23 |
| 2008/0294100 A1 * | 11/2008 | de Costa et al. | 604/84 |

* cited by examiner

*Primary Examiner* — Nicholas D Lucchesi
*Assistant Examiner* — Leah Stohr
(74) *Attorney, Agent, or Firm* — Jones Day

(57) ABSTRACT

A drug delivery system includes an automatic injector that can deliver a small, precise amount of a therapeutic agent. The automatic injector includes a chamber for containing a liquid component and a thin porous member that carries thereon and/or therein the small, precise amount of therapeutic agent. Upon activation of the automatic injector, a flow path opens from the chamber through the porous member, enabling the liquid component to rapidly mix with the therapeutic agent before being injected.

51 Claims, 14 Drawing Sheets

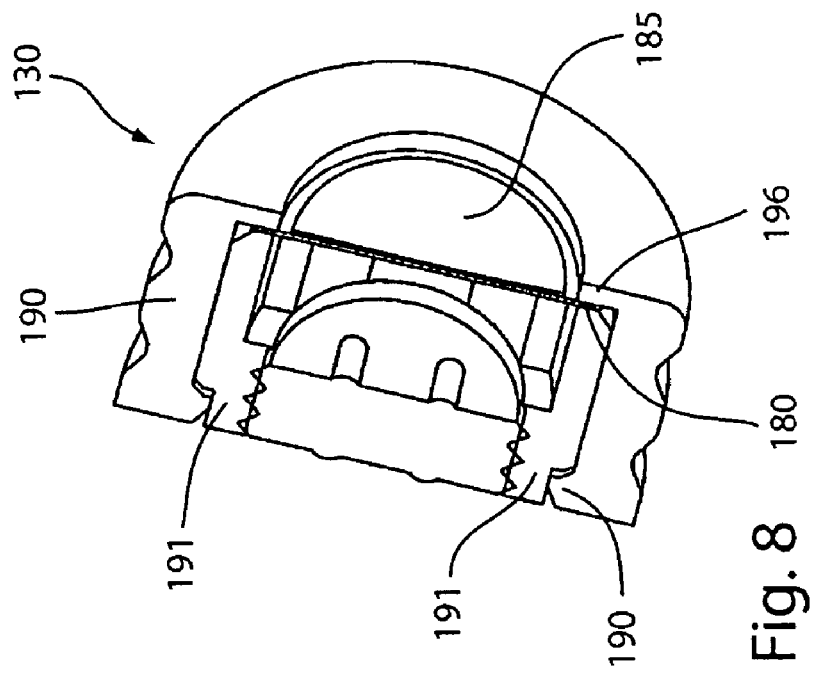
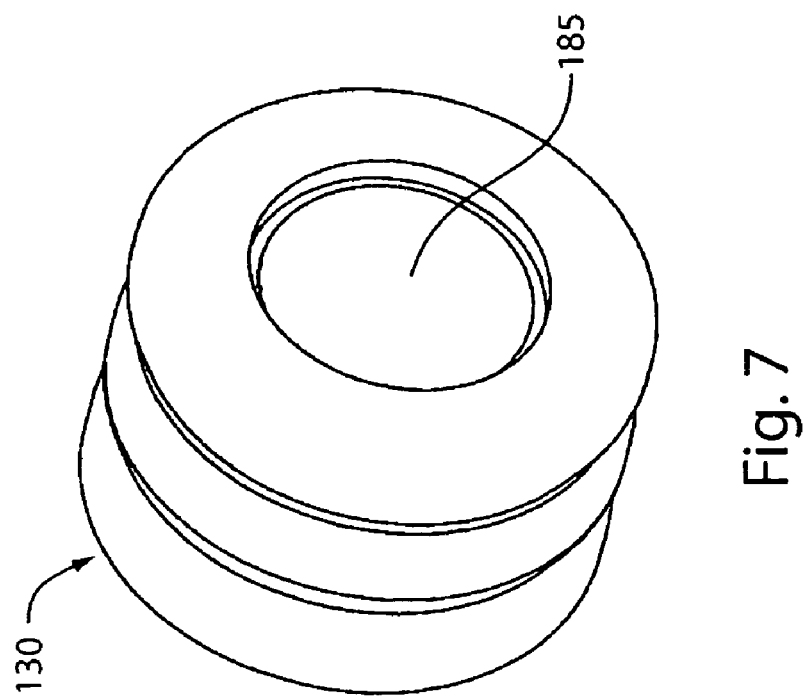

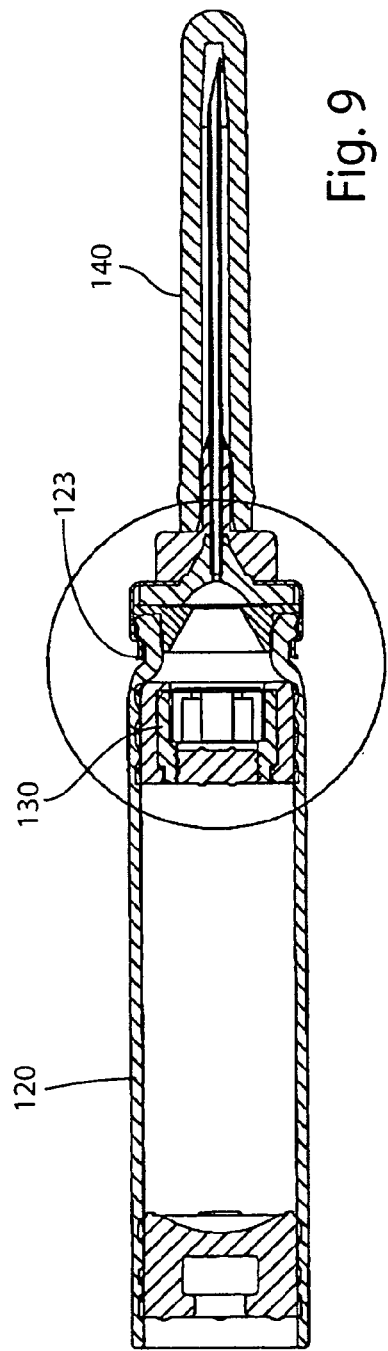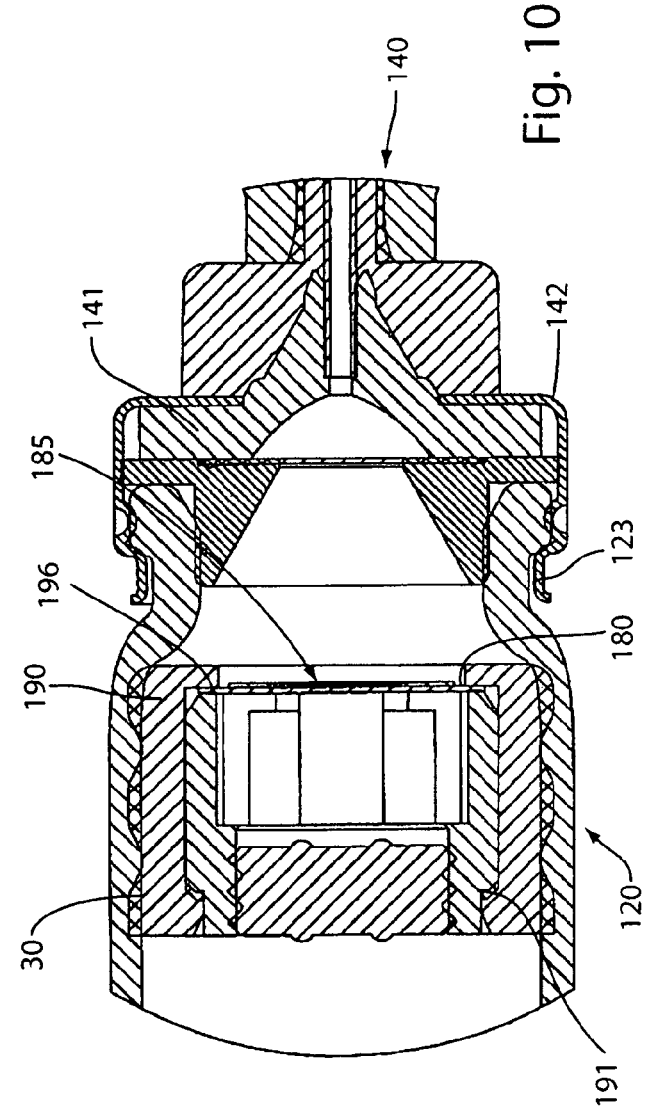

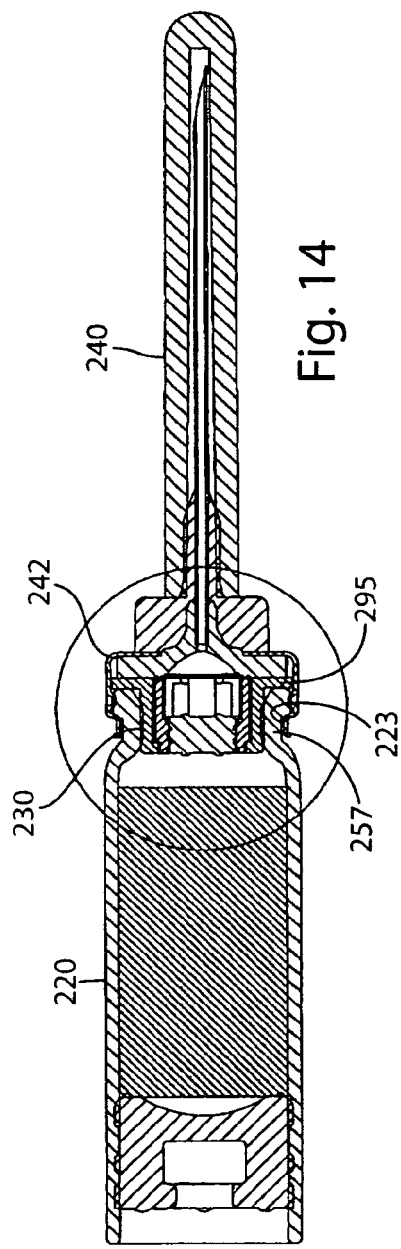
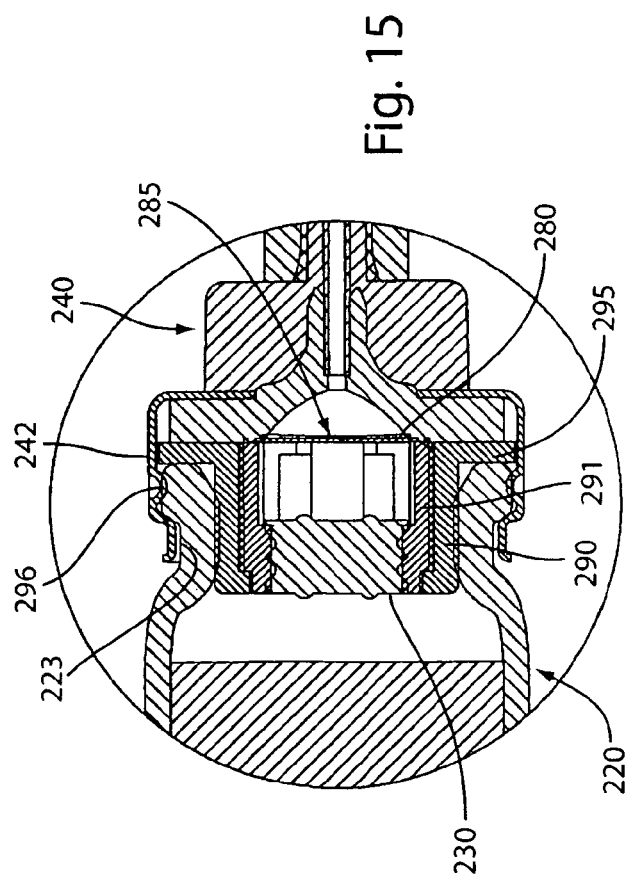

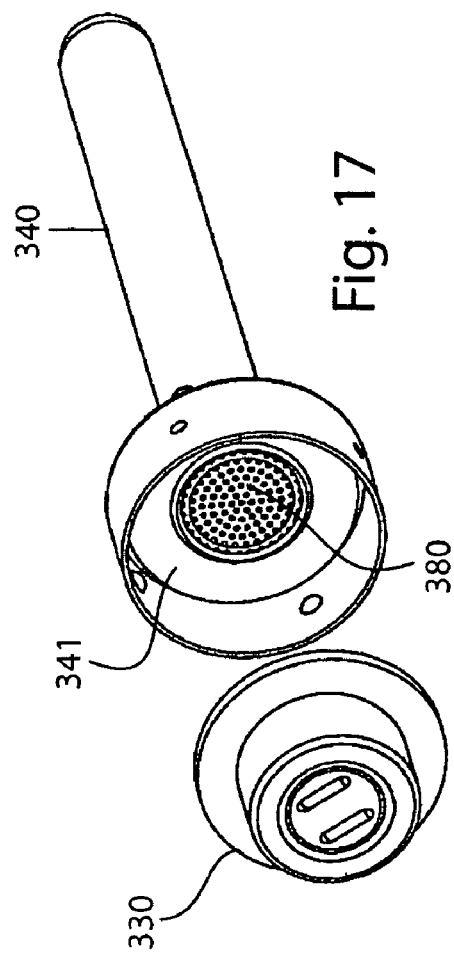
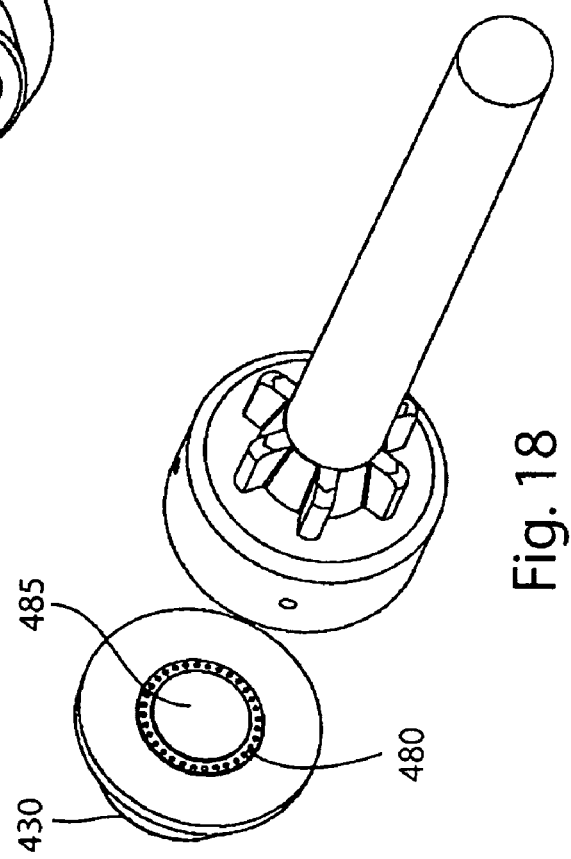

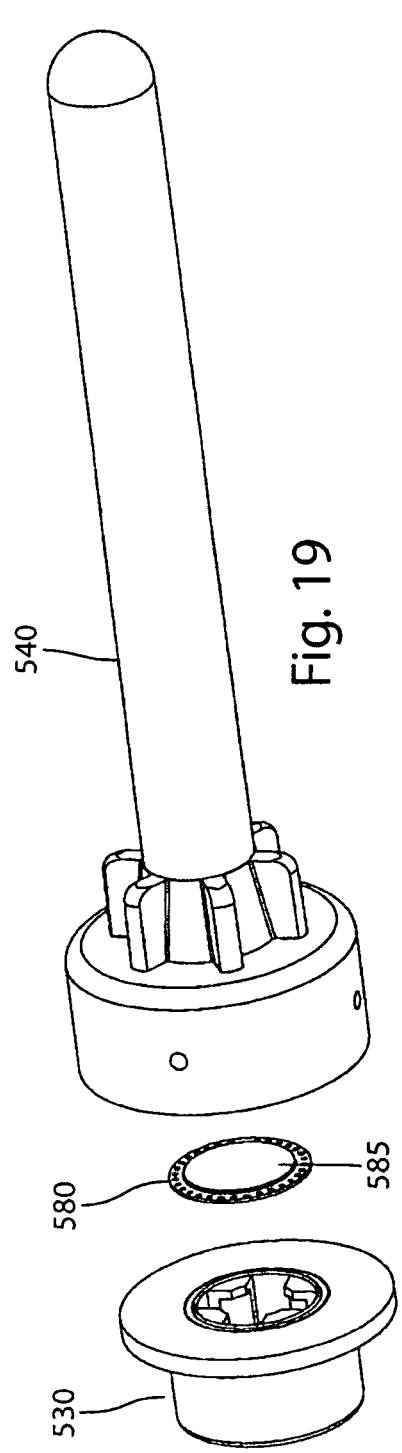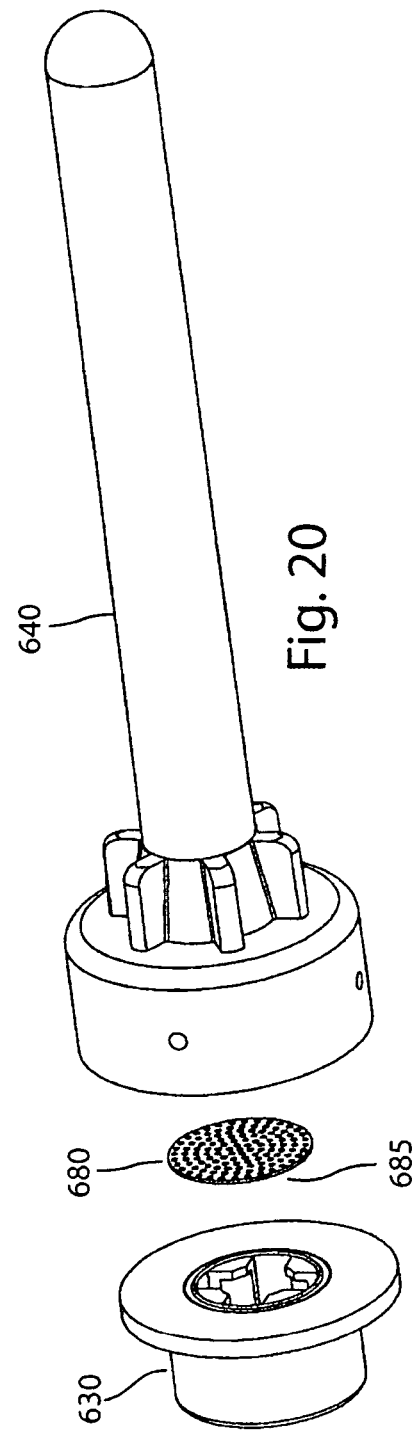

DRUG DELIVERY SYSTEM WITH A SMALL AMOUNT OF A THERAPEUTIC AGENT

CROSS REFERENCE TO RELATED APPLICATION

This claims the benefit of U.S. Provisional Application No. 60/928,594, filed May 9, 2007, the entire contents of which are incorporated herein by reference thereto.

FIELD OF THE INVENTION

The invention relates to drug delivery devices that deliver therapeutic agents. In particular, the invention is directed to automatic injection devices (also known as automatic injectors or auto-injectors) that can accommodate and deliver a small, precise amount of a therapeutic agent.

BACKGROUND OF THE INVENTION

An automatic injector is a device that performs intramuscular or subcutaneous administration of a therapeutic agent. An advantage of automatic injectors is that they contain a measured dose of a therapeutic agent in a sealed sterile cartridge. Automatic injectors can therefore be used in emergency situations to quickly and simply inject the therapeutic agent without having to measure dosages. Another advantage of automatic injectors is that the administration of the therapeutic agent is accomplished without the user initially seeing the hypodermic needle through which the therapeutic agent is delivered. Still another advantage is that the user does not have to manually force the needle into the patient. This is particularly advantageous when the therapeutic agent is being self-administered.

In some automatic injectors, the therapeutic agent is stored as a liquid solution. However, the long-term storage of a therapeutic agent in liquid term is problematic. For instance, some therapeutic agents in liquid form are not stable and thus have a shorter shelf-life than their solid counterparts. To address this concern, automatic injectors have been developed that store the therapeutic agent in solid form and, immediately prior to injection, mix the solid therapeutic agent with a liquid injection solution also stored in the injector. Such devices are generally referred to as wet/dry injectors. An example of such an injector is found in U.S. Reissue Pat. No. RE 35,986, entitled "Multiple Chamber Automatic Injector," the disclosure of which is incorporated herein by reference. These injectors require the user to manually rupture a sealing member between the solid and liquid components and then manually shake the injector body to expedite dissolution of the solid component prior to injection. Unfortunately, steps such as manually shaking the injector increase the time needed to administer a dose of the therapeutic agent, which is undesirable in many emergency medical situations where rapid delivery of the therapeutic agent is needed (e.g., in nerve gas and chemical agent poisoning).

Additionally, many of the wet/dry devices available are not capable of storing or delivering a small, precise amount of a therapeutic agent even though many therapeutic agents are effective at very small doses. For example, a therapeutically effective dosage of epinephrine may be about 0.1 mg to about 0.5 mg. In known wet/dry devices, however, the dry chamber that accommodates the therapeutic agent is relatively large. In order to effectively fill the dry chamber to ensure effective mixing, a greater amount of the therapeutic agent should be loaded into the chamber, which is costly and potentially dangerous to the person receiving the injection. Alternatively, various excipients may be added to the therapeutic agent to effectively fill the dry chamber. However, adding excipients to a therapeutic agent requires additional expense and manufacturing in order to formulate and produce the therapeutic agent with the excipients prior to the agent being loaded into an injector.

Therefore, a need exists for a cost-effective automatic injector that can store a small, precise amount of a therapeutic agent and that does not require manual premixing by the user.

SUMMARY OF THE INVENTION

The invention provides a cost-effective automatic injector capable oil accommodating and delivering a small, precise amount of a therapeutic agent to a user without manual premixing. In particular, the invention provides an automatic injector that has a thin or flat porous member carrying the small, precise amount of the therapeutic agent. This porous member advantageously does not require additional space within the injector, and thus the space typically required for a second, dry compartment common in wet/dry auto-injectors, and/or the space typically required for bulky scaffolds, substrates, sponges, cell structures, and tubular networks that hold therapeutic agents in some known injection devices, can be reduced in size, if not eliminated, from the injector. While existing automatic injectors may be able to use the porous member of the invention without significant re-design or modification, automatic injectors of the invention are advantageously shorter and/or more compact than existing automatic injectors.

One embodiment of the invention includes an automatic injector that has an interior chamber containing a liquid injection component, a seal structure inserted into an open end of the chamber, a needle assembly mounted to the open end of the chamber, a thin porous member located between the seal structure and the needle assembly, and a therapeutic agent disposed on and/or in the porous member. The seal structure has a first state that seals the liquid component in the chamber and a second state that allows the liquid component to flow from the chamber through the seal structure. The seal structure and the thin porous member may be integrated into a single assembly, or alternatively, the porous member and the needle assembly may be integrated into a single assembly. Either integration can be accomplished by any known means in the art, such as, for example, the porous member may be sonically welded to the seal structure or to the needle assembly.

Another embodiment of the invention is a method of assembling an automatic injector containing a therapeutic agent. The method includes filling a chamber with a liquid injection component and inserting a seal structure into the chamber. The seal structure is convertible from a sealing condition, which seals the liquid component in the chamber, to a flow-through condition, which allows the liquid component to flow out of the chamber through a flow path. The method also includes applying a therapeutic agent to a flat porous member, securing the flat porous member containing the therapeutic agent at or after the end of the flow path, and mounting a needle assembly onto the chamber to dispense the therapeutic agent mixed with the liquid component.

The term "thin" as used herein to describe the porous member is defined as having little extent from one surface to its opposite surface (i.e., its thickness). Similarly, the term "flat" as used herein to describe the porous member is defined as having little or no illusion of depth or thickness. For example, in one embodiment of the invention, the diameter or width of the porous member extending across the flow path (that is, measured in the lateral direction of the chamber) is about 0.30 inches (7.62 mm), while the thickness of the porous member (measured in the longitudinal direction of the chamber) preferably ranges from only about 0.005 inches (0.13 mm) to about 0.020 inches (0.51 mm).

The amount of therapeutic agent carried by the porous member is preferably less than or equal to about 25 mg. The therapeutic agent may be, for example, epinephrine. The porous member has a plurality of pores or holes, wherein the average pore width or diameter preferably ranges from about 0.02 microns to about 5 microns. The therapeutic agent carried by the porous member is either disposed on a surface of the porous member and/or contained within the porous member (i.e., disposed within the pores). The porous member has a surface facing the needle assembly and a surface facing the seal structure. The therapeutic agent is preferably disposed on at least one of those surfaces and may be disposed on both. Alternatively or additionally, the therapeutic agent may be disposed within at least some of the pores of the porous member.

The porous member may be made of a metallic material, a polymeric material, a ceramic material, or combinations thereof. The porous member may be, for example, a filter, a polymeric membrane, or a metal disc.

Another embodiment of the invention includes an automatic injector having an interior chamber with an open end, a seal structure positioned in the chamber, a needle assembly mounted to the chamber at the open end, a filter or membrane positioned either at the seal structure, at the needle assembly, or between the seal structure and needle assembly, and a therapeutic agent carried by the filter or membrane. The interior chamber contains a liquid injection component, and the seal structure converts from a sealing condition to a flow-through condition. The flow-through condition allows the liquid component to flow out of the chamber through a flow path to the needle assembly. The filter or membrane has an area that extends across the flow path and a negligible thickness and volume. The amount of therapeutic agent carried by the filter or membrane is preferably less than or equal to about 25 mg.

The term "negligible" as used herein to describe the thickness and volume of the filter or membrane is defined as being so small or unimportant as to warrant little or no attention— especially with respect to providing space for the filter or membrane within an automatic injector.

BRIEF DESCRIPTION OF THE DRAWINGS

The features and advantages of the invention will be apparent upon consideration of the following detailed description, taken in conjunction with the accompanying drawings, in which like reference characters refer to like parts throughout, and in which:

FIGS. 5-8 are lateral, longitudinal cross-sectional, perspective, and perspective cross-sectional views, respectively, of the seal structure of FIGS. 1, 3, and 4;

FIGS. 9 and 10 are longitudinal and enlarged, partial longitudinal cross-sectional views of the assembled chamber, seal structure, and needle assembly of the injector of FIG. 1;

FIGS. 14 and 15 are longitudinal and enlarged, partial longitudinal cross-sectional views of the assembled chamber, seal structure, and needle assembly of the injector of FIG. 11;

FIGS. 17-20 are various perspective views of seal structures porous members, and needle assemblies according to the invention.

DETAILED DESCRIPTION OF THE INVENTION

The invention is directed to automatic injectors that can accommodate and deliver a small, precise amount of a therapeutic agent. The automatic injectors include a thin or flat porous member that carries thereon and/or therein the therapeutic agent. Advantageously, the thin or flat porous member with the therapeutic agent thereon and/or therein results in a shorter, more compact injection device because most, if not all, of the space needed for either (1) a second, dry compartment common in wet/dry automatic injectors or (2) the various types of known generally cylindrically-shaped scaffolds, substrates, sponges, cell structures, and tubular networks used to hold therapeutic agents in known injectors is unnecessary.

The invention is not limited to any one type of automatic injector. For example, the invention may include a nose activated auto-injector, as described, for example, in U.S. Pat. No. 5,354,286, the disclosure of which is incorporated by reference. The invention may alternatively include a push button type auto-injector, where the user removes an end cap and presses a button to trigger the injection process as described, for example, in U.S. Pat. No. 6,641,561, the disclosure of which is also incorporated by reference.

Figure 1:
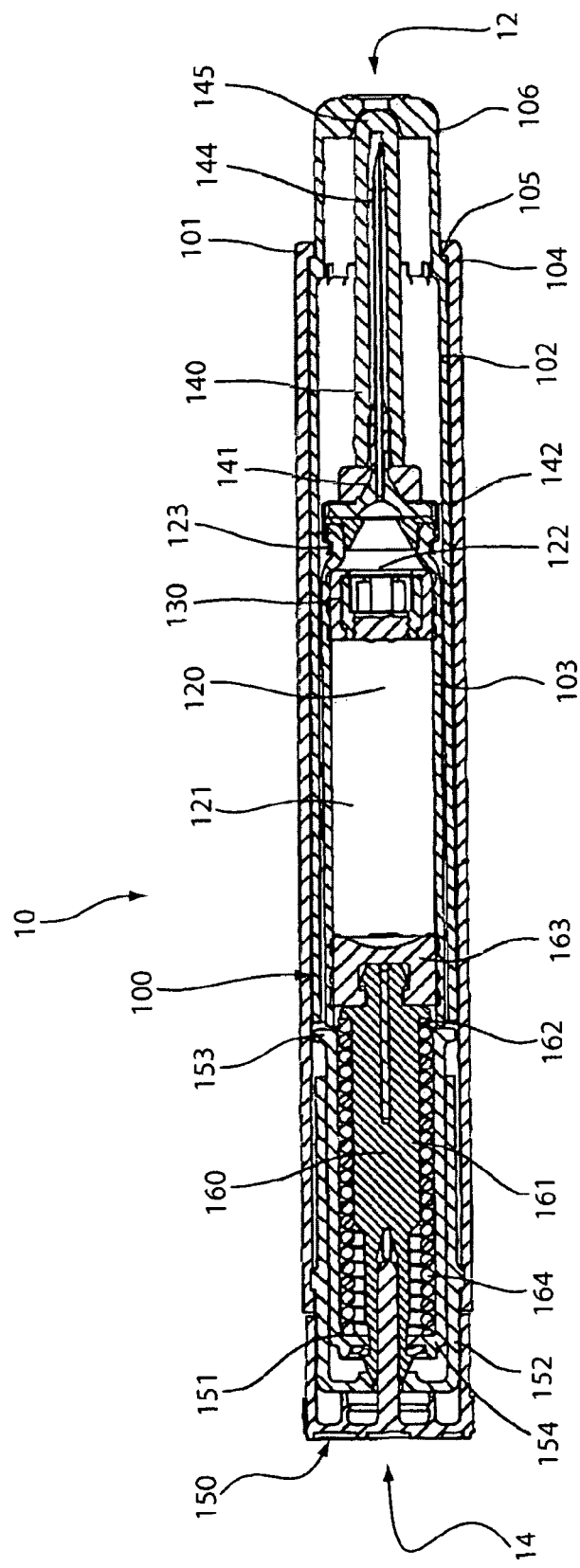
FIG. 1 is a longitudinal cross-sectional view of an automatic injector according to the invention.

FIG. 1 shows an embodiment of an automatic injector that can be used in connection with the invention. Automatic injector 10 has a needle end 12 and an activation end 14. The device has an outer body or housing 100 having an in-turned shoulder 101. Located within the interior of outer body 100 is a cartridge holder 102. Cartridge holder 102 has a shoulder 104 that fits against seat 105 of in-turned shoulder 101. Cartridge holder 102 also has a forward end portion 106 that is tapered to form a small circular aperture. Received within cartridge holder 102 is a cartridge assembly 103. The overall length of cartridge assembly 103 is completely contained within cartridge holder 102. Cartridge assembly 103 has a chamber 120 that is preferably a hollow cylinder with either a smooth cylindrical interior surface or smooth interior side walls. Chamber 120 has a first compartment 121 and, optionally, a much smaller second compartment 122. Preferably, the liquid injection solution or component is located within first compartment 121. A seal structure 130 engages the interior surface or side walls of chamber 120 to seal the liquid injection solution in first compartment 121 and prevent seepage of the liquid injection solution into the optional second compartment 122 prior to activation of the injector device.

A needle assembly 140 is mounted to the forward end of chamber 120 to inject the therapeutic agent into a user upon activation of the injector. In this embodiment, the forward end portion of chamber 120 has an annular groove 123 formed therein for attachment of needle assembly 140. Needle assembly 140 has a crimp clamp 142 that is mechanically rolled into annular groove 123 to permanently secure and seal the needle assembly to the chamber. Needle assembly 140 also includes a funnel-shaped needle support 141, which can be made of a resilient plastic material or a metal with a rubber seal. Needle support 141 forms a sealed fluid channel from chamber 120 to needle 144. A rubber needle sheath 145 surrounds needle 144 and receives the narrow end of needle support 141.

In addition to cartridge holder 102 and needle assembly 140, outer body 100 also includes a stored energy assembly 150. The stored energy assembly can be any conventional type known in the art, such as the forward end activating device disclosed in U.S. Pat. No. 3,712,301, the disclosure of which is incorporated by reference. In another example, rather than employing a spring, the stored energy assembly may employ a charge of compressed gas.

As shown in FIG. 1, stored energy assembly 150 has an inner sleeve 151 and an outer sleeve 152. Inner sleeve 151 has an out-turned flange 153 and an end wall 154. Out-turned flange 153 fits up against the end of cartridge holder 102 when the stored energy assembly is inserted into outer body 100. Note that the length of outer sleeve 152 is slightly less than that of inner sleeve 151 in order to leave space between the wall of outer sleeve 152 and flange 153 of inner sleeve 151. Stored energy assembly 150 also has a collet 160 that fits within out-turned flange 153 of inner sleeve 151. The collet has a body portion 161 and a head portion 162. The diameter of head portion 162 is larger than body portion 161 and is generally slightly smaller than that of a plunger 163. A coil spring 164 is positioned over collet body portion 161 and abuts head portion 162 at one end and abuts the inner face of end wall 154 of inner sleeve 151 at the other end.

Figure 2:
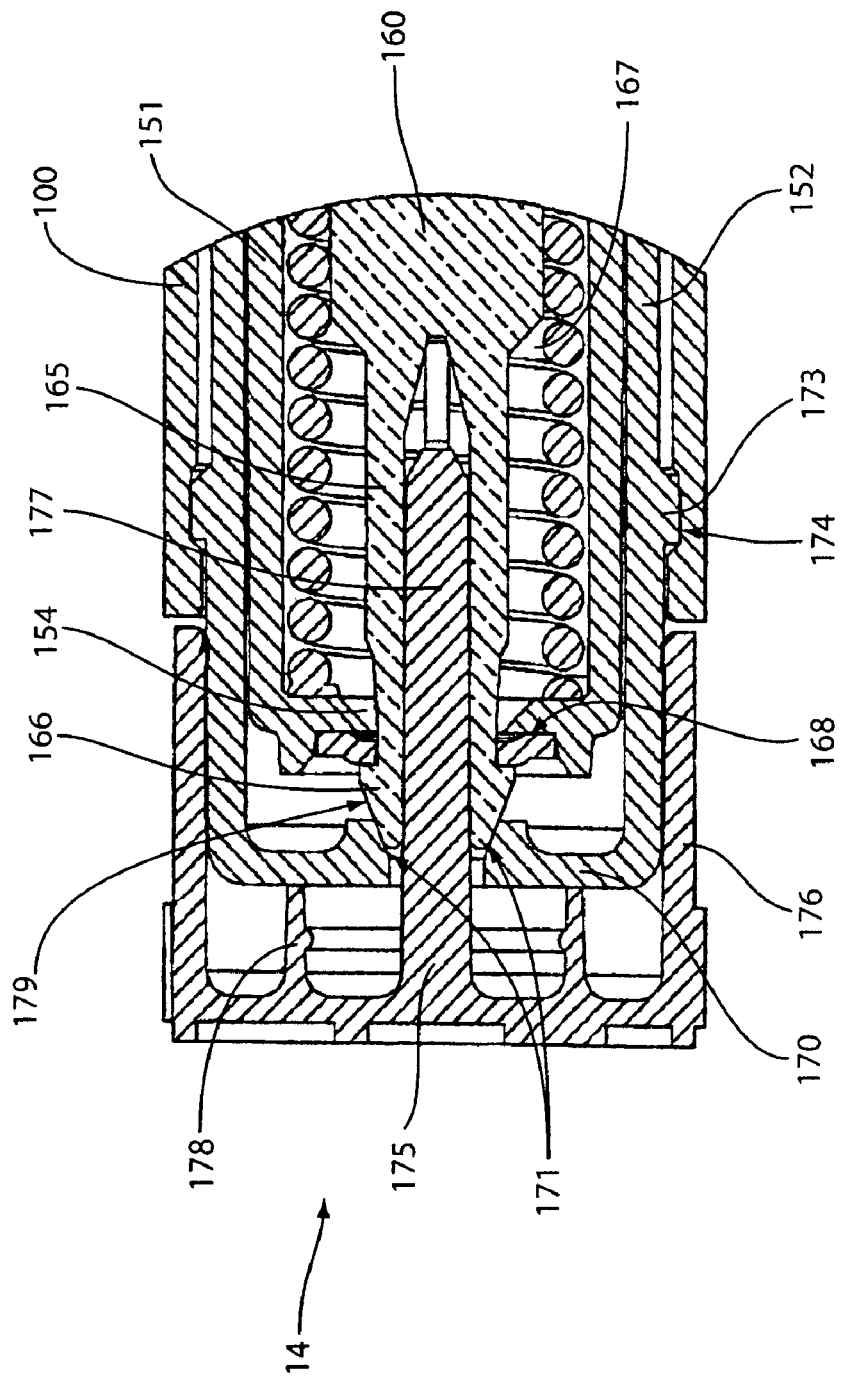
FIG. 2 is an enlarged, longitudinal cross-sectional view of the activation end of the automatic injector of FIG. 1.

FIG. 2 shows activation end 14 of the automatic injector of FIG. 1. Collet 160 has four equally-spaced, longitudinally extending spring fingers 165 terminating in frusto-conical, locking detent heads 166. These locking detent heads maintain collet 160 and inner sleeve 151 in an assembled position with a coil spring 167 compressed there between. Upon compression of coil spring 167, detent heads 166 are cammed inwardly by engaging the periphery of the end wall 154 opening so they can be passed through that opening, whereupon the bases of detent heads 166 come to rest on retaining surface 168 of end wall 154 to retain collet 160 and inner sleeve 151 in assembled condition with coil spring 167 compressed there between. When desired, the rear planar surface of the inner sleeve can be advantageously overlaid with a metal washer providing a guide and a holding flange to surround the opening.

Outer sleeve 152 has a closed end 170 with a central aperture from which a frusto-conical surface 171 extends. Surface 171 is sized and shaped to cooperate with frusto-conical detent heads 166 to cam the heads radially inward. The outer sleeve 152 is provided with a circumferential locking rib 173 that fits in an annular groove 174 in outer body 100 to retain the stored energy assembly in position in the outer body. As noted above, the length of outer sleeve 152 is slightly less than that of inner sleeve 151 in order to leave space between the inner wall of outer sleeve 152 and flange 153 of inner sleeve 151. This allows the two sleeves to move relative to each other to cam frusto-conical detent heads 166 inwardly during operation of the device.

To make certain that the frusto-conical detent heads 166 are not accidentally cammed inwardly, a safety pin assembly 175 is provided. Safety pin assembly 175 has a cylindrical sleeve 176 sized to fit over the end portion of outer sleeve 152. A safety pin 177 extends inwardly from the center of safety pin assembly 175 into the opening formed by the inner portions of detent heads 166 to prevent inward movement of the detent heads. Safety pin assembly 175 is provided internally with a plurality of spacer abutments 178 to assure proper positioning of the cap on outer sleeve 152.

To activate the injector, safety pin assembly 175 is manually pulled off the rear end of the injector, thus removing pin 177 from between fingers 165. Needle end 12 of injector 10 is then pressed against an injection site. A telescoping action takes place between outer body 100 and cartridge holder 102. This telescoping action causes the sleeves of the stored energy assembly to telescope, which causes surfaces 171 of outer sleeve 152 to engage the sloping surface 179 of detent heads 166. This forces detent heads 166 inward toward one another and off of retaining surface 168 of end wall 154. Coil spring 167 is now free to release its stored energy. This moves collet 160 forward to effect an injection operation.

Figure 3:
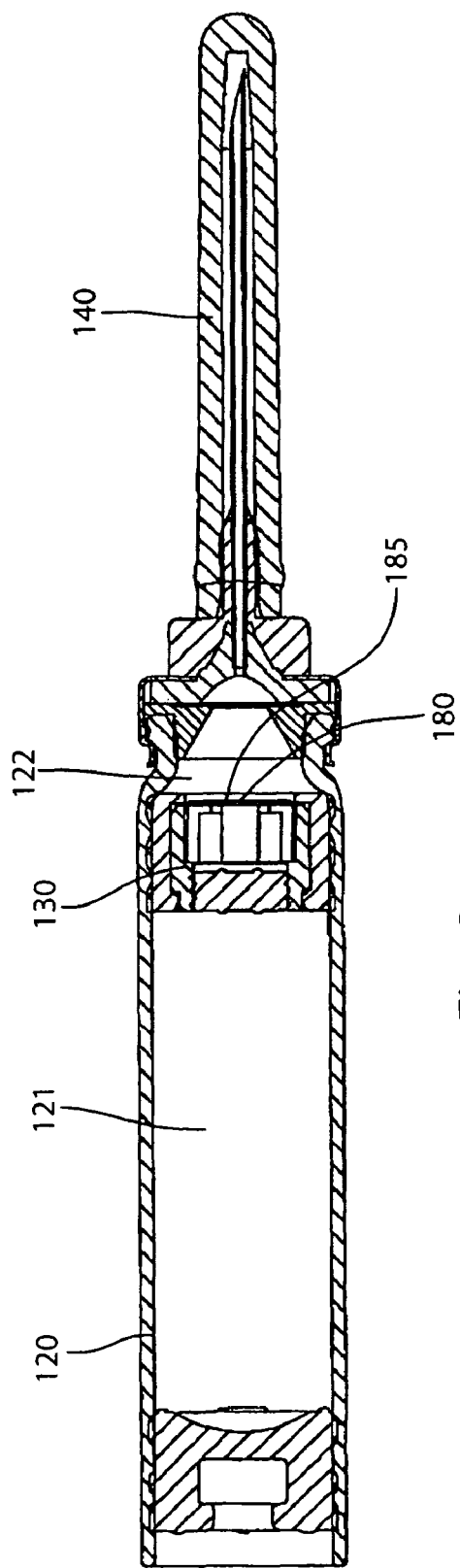
FIG. 3 is a longitudinal cross-sectional view of an assembled chamber, seal structure, and needle assembly of the injector of FIG. 1.

FIG. 3 shows an assembly of needle assembly 140 and chamber 120. In this embodiment, chamber 120 has a first compartment 121 and a significantly smaller second compartment 122 separated by seal structure 130. Liquid injection solution is stored in first compartment 121. Seal structure 130 engages the interior surface or side walls of chamber 120 to seal first compartment 121 from second compartment 122, thus preventing any liquid injection solution from entering second compartment 122. Adjacent seal structure 130 is a thin or flat porous member 180. Therapeutic agent 185 is disposed on a surface of porous member 180, which is positioned adjacent seal structure 130. The therapeutic agent may alternatively or additionally be disposed within the pores of the porous member.

Figure 4:
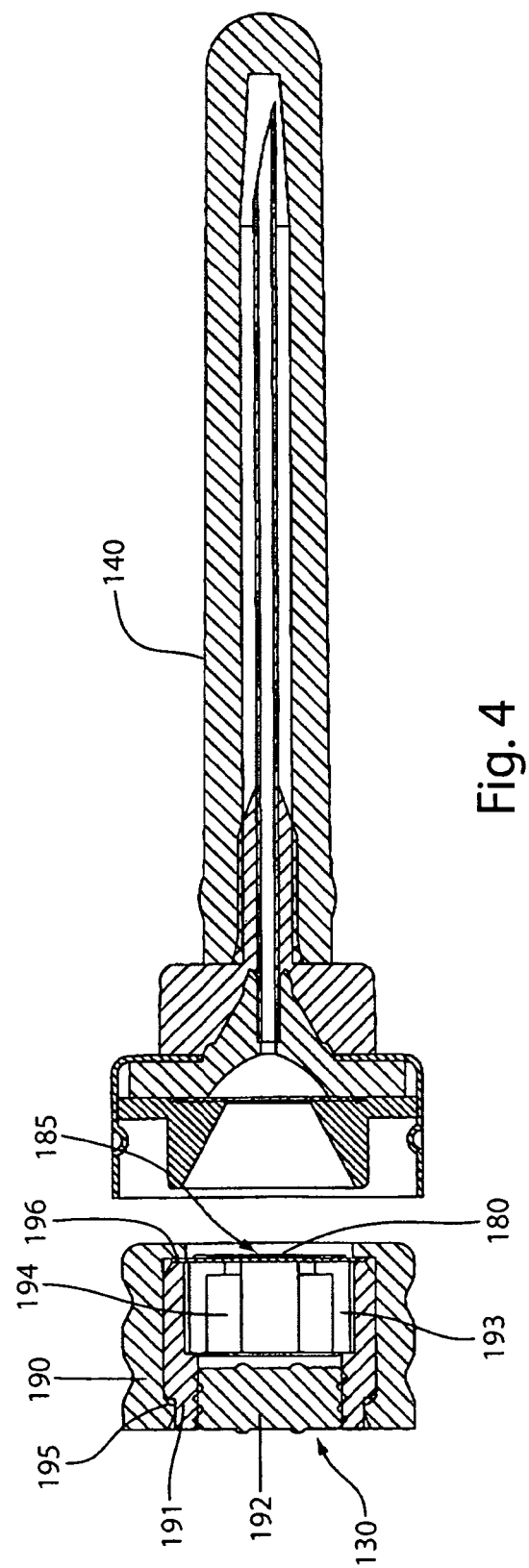
FIG. 4 is a longitudinal cross-sectional view of the seal structure and needle assembly of FIG. 3.
Figure 6:
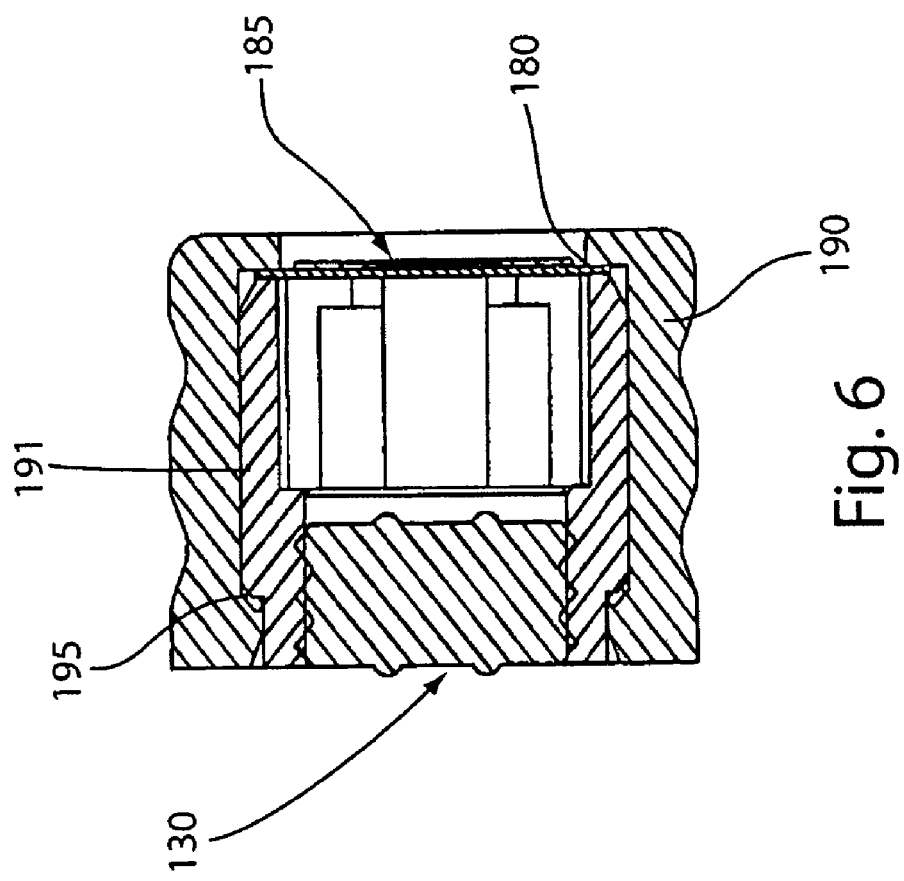
Figure 5:
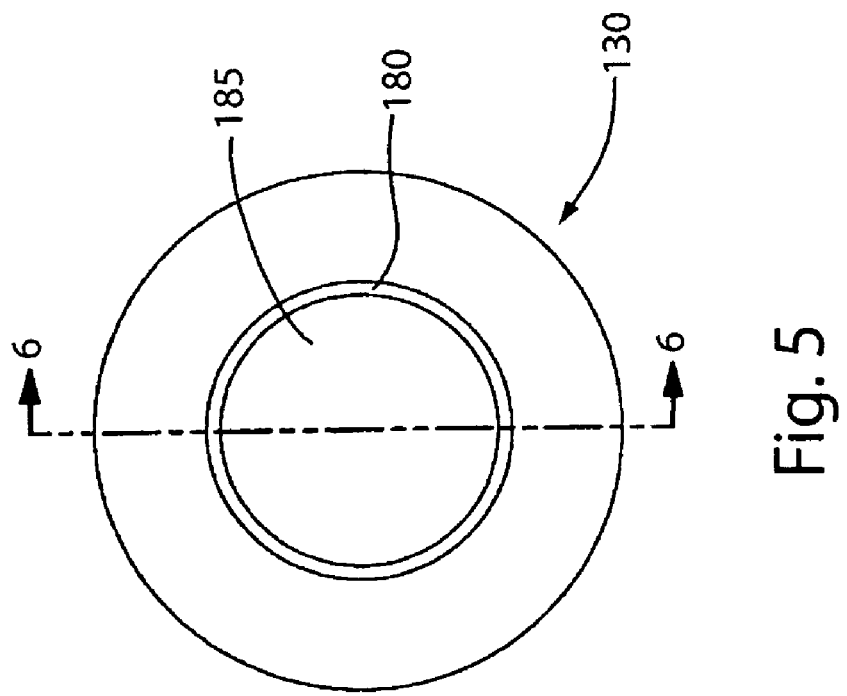

FIG. 4 shows seal structure 130 and needle assembly 140. Seal structure 130 has an outer seal 190, an internal rigid member 191, and a movable sealing plug 192. Outer seal 190 and internal rigid member 191 securely engage each other using a combination of notched recesses 195 and extending shoulders 196. In other embodiments, outer seal 190 and internal rigid member 191 may be secured together using bonding techniques known in the art or may be formed as an integral component. Internal rigid member 191 may also be formed from two rigid bodies (e.g., two halves) that are annularly welded or bonded together. Internal rigid member 191 has a by-pass channel 193 which creates at least one flow path. When plug 192 is moved from its location as shown in FIG. 4 to by-pass area 194, by-pass channel 193 becomes a flow path such that a liquid component can flow through both seal structure 130 and porous member 180, dissolving therapeutic agent 185.

FIGS. 5-8 show seal structure 130 and porous member 180 with a therapeutic agent 185 disposed on a surface of the porous member 180. Porous member 180 is held in place between internal rigid member 191 and shoulder 196 of outer seal 190 and may be welded or bonded to rigid member 191. In embodiments where the internal rigid member is formed from two rigid bodies, the porous member can be secured between those two rigid bodies. Therapeutic agent 185 is carried on the surface of porous member 180 that faces away from internal rigid member 191 (that is, on the front side of the porous member). In alternative embodiments, the therapeutic agent can be disposed on the surface facing the rigid member or on both surfaces of the porous member. In still other embodiments, the therapeutic agent can be located within the plurality of pores or holes in the porous member or within the pores/holes and on one or both of the surfaces of the porous member.

FIGS. 9 and 10 show the assembly of chamber 120, seal structure 130, and needle assembly 140. Chamber 120 contains seal structure 130, which has an outer seal 190 and an internal rigid member 191. Outer seal 190 forms an annular seal with the inner surface of chamber 120 to prevent liquid from seeping around the seal structure. Porous member 180, which contains therapeutic agent 185, is held in place between internal rigid member 191 and shoulder 196 of outer seal 190 and may be welded or bonded to rigid member 191. The forward end portion of chamber 120 has an annular groove 123 formed therein about which needle assembly 140 is mounted. Needle assembly 140 preferably includes a needle support 141, which includes at least one crimp clamp 142. Crimp clamp 142 is mechanically rolled into groove 123 to secure and seal needle assembly 140 to chamber 120.

Figure 11:
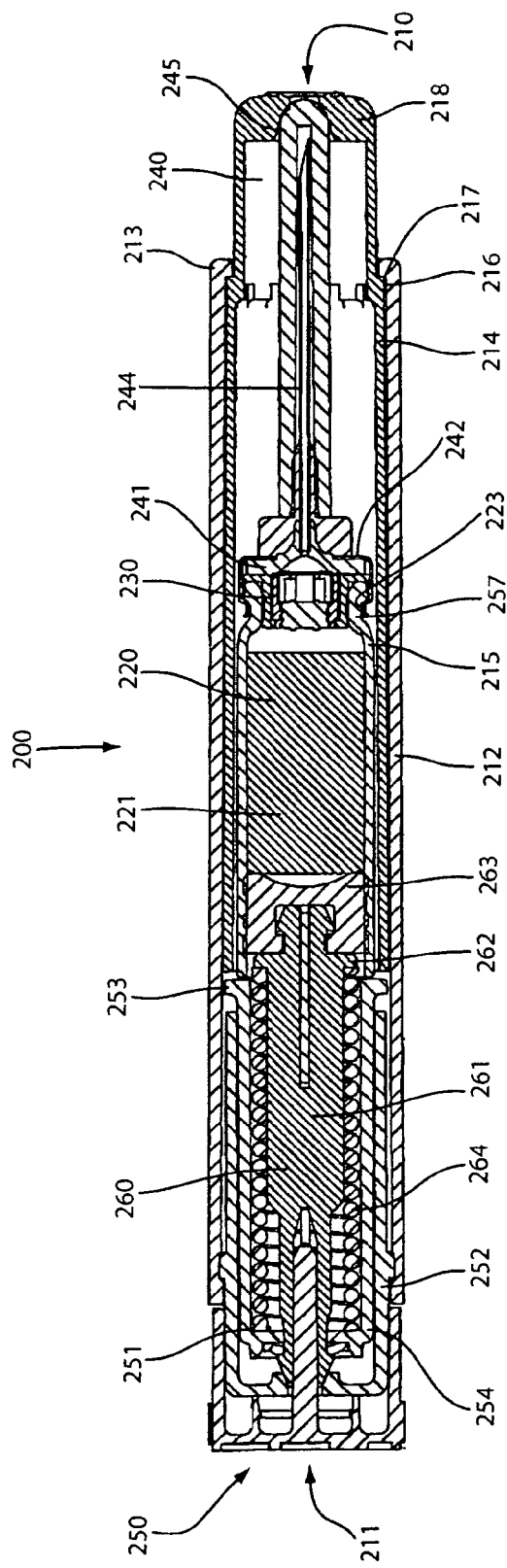
FIG. 11 is a longitudinal cross-sectional view of another embodiment of an automatic injector according to the invention.

FIG. 11 shows another embodiment of an automatic injector that can be used in connection with the invention. Automatic injector 200 has a needle end 210 and an activation end 211. The device has an outer body or housing 212 that has an in-turned shoulder 213. Located within the interior of outer body 212 is a cartridge holder 214. Cartridge holder 214 has a shoulder 216 which fits against seat 217 of in-turned shoulder 213. Cartridge holder 214 also has a forward end portion 218 that is tapered to form a small circular aperture. Received within cartridge holder 214 is a cartridge assembly 215. The overall length of cartridge assembly 215 is completely contained within cartridge holder 214. Cartridge assembly 215 has a chamber 220 that is preferably a hollow cylinder with either a smooth cylindrical inner surface or smooth interior side walls. In this embodiment, chamber 220 has a single compartment 221 that can contain a liquid injection solution or component. Advantageously, there is no second compartment. A seal structure 230 engages the inner surface or interior side walls of chamber 220 to seal compartment 221 and prevent seepage of the liquid injection solution prior to activation of the injector device.

Further, a needle assembly 240 mounts to chamber 220 to inject the therapeutic agent upon activation of the injector device. The forward end portion of chamber 220 has an annular groove 223 formed therein for attachment of needle assembly 240. Needle assembly 240 includes a funnel-shaped needle support 241 that has a crimp clamp 242 mechanically rolled into annular groove 223 to permanently secure and seal the needle assembly to the chamber. Needle support 241 can be made of a resilient plastic material or a metal with a rubber seal. Needle support 241 forms a sealed fluid channel from chamber 220 to needle 244. A rubber needle sheath 245 surrounds needle 244 and receives the narrow end of needle support 241.

In addition to cartridge holder 214 and needle assembly 240, outer body 212 includes a stored energy assembly 250. The stored energy assembly can be any conventional type known in the art, such as the forward end activating device disclosed in U.S. Pat. No. 3,712,301. In another example, rather than employing a spring, the stored energy assembly may employ a charge of compressed gas.

As shown in FIG. 11, stored energy assembly 250 has an inner sleeve 251 and an outer sleeve 252. Inner sleeve 251 has an out-turned flange 253 and an end wall 254. Out-turned flange 253 fits up against the end of cartridge holder 214 when the stored energy assembly is inserted into outer body 212. Note that the length of outer sleeve 252 is slightly less than that of inner sleeve 251 in order to leave space between the wall of outer sleeve 252 and flange 253 of inner sleeve 251.

Stored energy assembly 250 also has a collet 260 that fits within out-turned flange 253 of inner sleeve 251. The collet has a body portion 261 and a head portion 262. The diameter of head portion 262 is larger than body portion 261 and is generally slightly smaller than that of a plunger 263. A coil spring 264 is positioned over collet body 261 and abuts head portion 262 at one end and abuts the inner face of end wall 254 of inner sleeve 251 at the other.

A significant difference between the automatic injector of FIG. 1 and that of FIG. 11 is the location of the seal structure. In FIG. 1, seal structure 130 is located in the main, large diameter portion of chamber 120, while in FIG. 11, seal structure 230 is alternatively located in a neck portion 257 of chamber 220.

Figure 12:
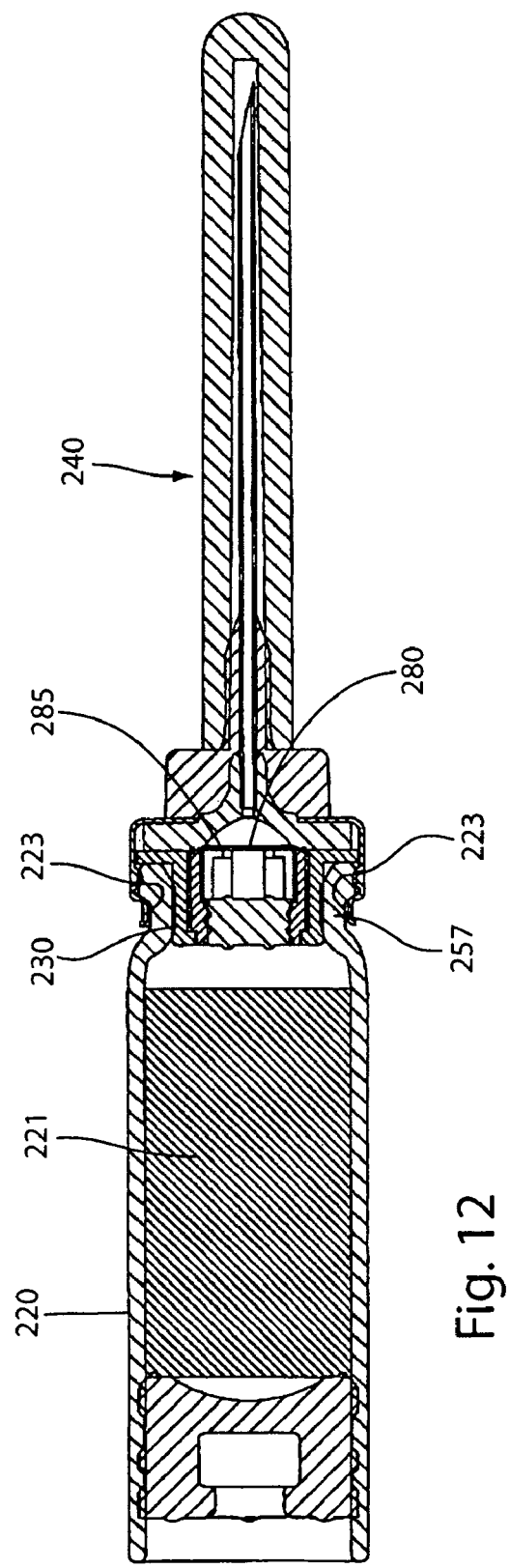
FIG. 12 is a longitudinal cross-sectional view of another embodiment of an assembled chamber, seal structure, and needle assembly of the injector of FIG. 11.

FIG. 12 shows an assembly of chamber 220, seal structure 230, and needle assembly 240 of automatic injector 200. The chamber has neck portion 257, which has an annular groove 223. Seal structure 230 engages the inner surface or interior side walls of neck portion 257 and is adjacent annular groove 223. Therapeutic agent 285 is disposed on porous member 280, which is located on seal structure 230. The seal structure seals and prevents any liquid stored in compartment 221 from contacting the therapeutic agent prior to activation of the automatic injector.

Figure 13:
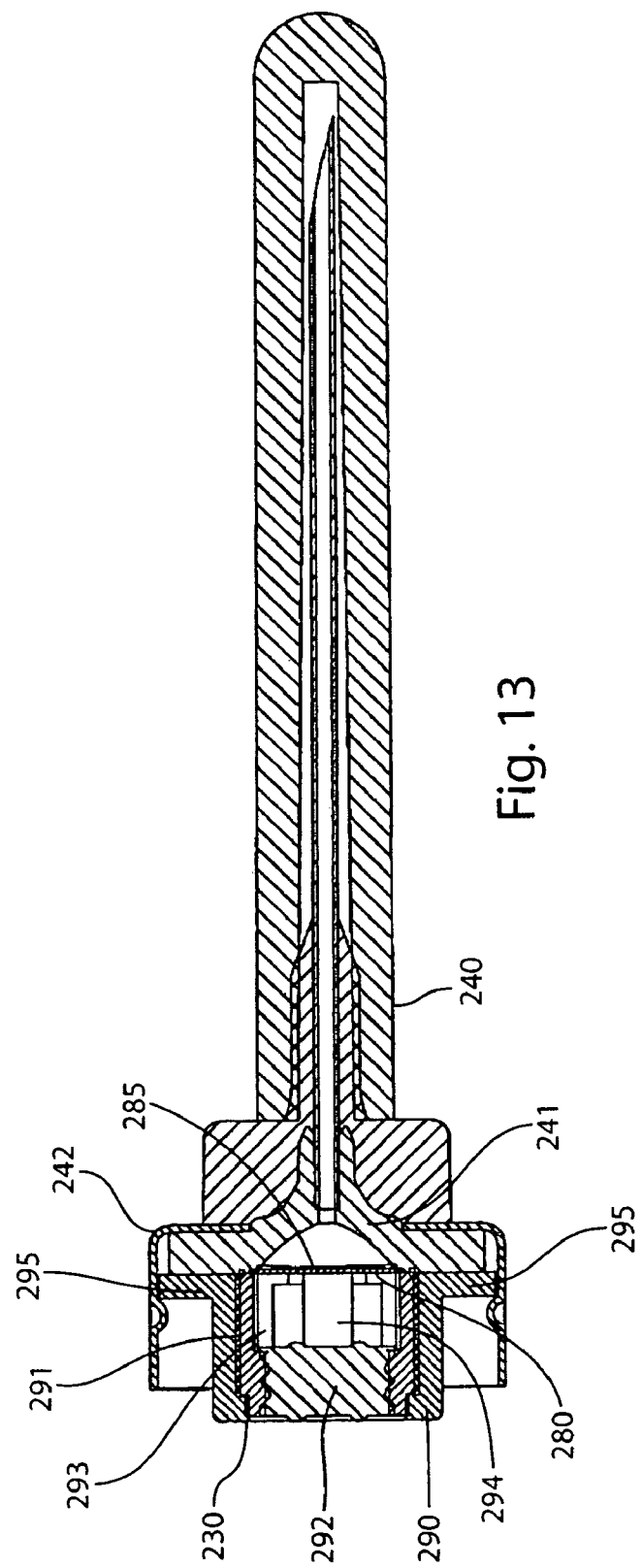
FIG. 13 is a longitudinal cross-sectional view of the assembled seal structure and needle assembly of FIG. 12.

FIG. 13 shows seal structure 230 and needle assembly 240. Seal structure 230 has an outer seal 290, an internal rigid member 291, and a movable sealing plug 292. Outer seal 290 includes at least one side flange 295. Seal structure 230 is secured to needle assemble 240 by fitting side flange 295 into crimp clamp 242. Seal structure 230 also includes thin or flat porous member 280, which contains therapeutic agent 285. Porous member 280 is held in place between outer seal 290 and needle support 241 and may be welded or bonded to rigid member 291. Alternatively, the porous member may be secured in place between the outer seal and the internal rigid member and, in those embodiments where the internal rigid member is formed from two rigid bodies (e.g., two halves) that are annularly welded or bonded together, the porous member may be secured between those two rigid bodies. Internal rigid member 291 has a by-pass channel 293 which creates at least one flow path. When plug 292 is moved from its location as shown in FIG. 13 to by-pass area 294, by-pass channel 293 opens a flow path that allows the liquid component to flow through both seal structure 130 and porous member 280.

FIGS. 14 and 15 show the assembly of chamber 220, seal structure 230, and needle assembly 240. Chamber 220 has neck portion 257 and annular groove 223. Seal structure 230 is located in neck portion 257 and has at least one side flange 295. Note that, in contrast, seal structure 130 of injector 100 does not have a side flange. Needle assembly 240 mounts to chamber 220 by rolling crimp clamp 242 into groove 223, further securing side flange 295 between chamber 220 and needle assembly 240. Within chamber 220 is seal structure 230, which has an outer seal 290 and an internal rigid member 291. Outer seal 290 includes side flange 295. Seal structure 230 is temporarily held in position between chamber 220 and needle assemble 240 when annular ridge member 296 is press fit to the flange of chamber 220, thereby securing flange 295 between chamber 220 and needle assemble 240. The lower portion of clamp 242 is rolled into groove 223 of chamber 220 securing flange 295 between chamber 220 and needle assembly 240. In this embodiment, porous member 280, which contains therapeutic agent 285, is ultrasonically welded to ridge member 291.

Figure 16:
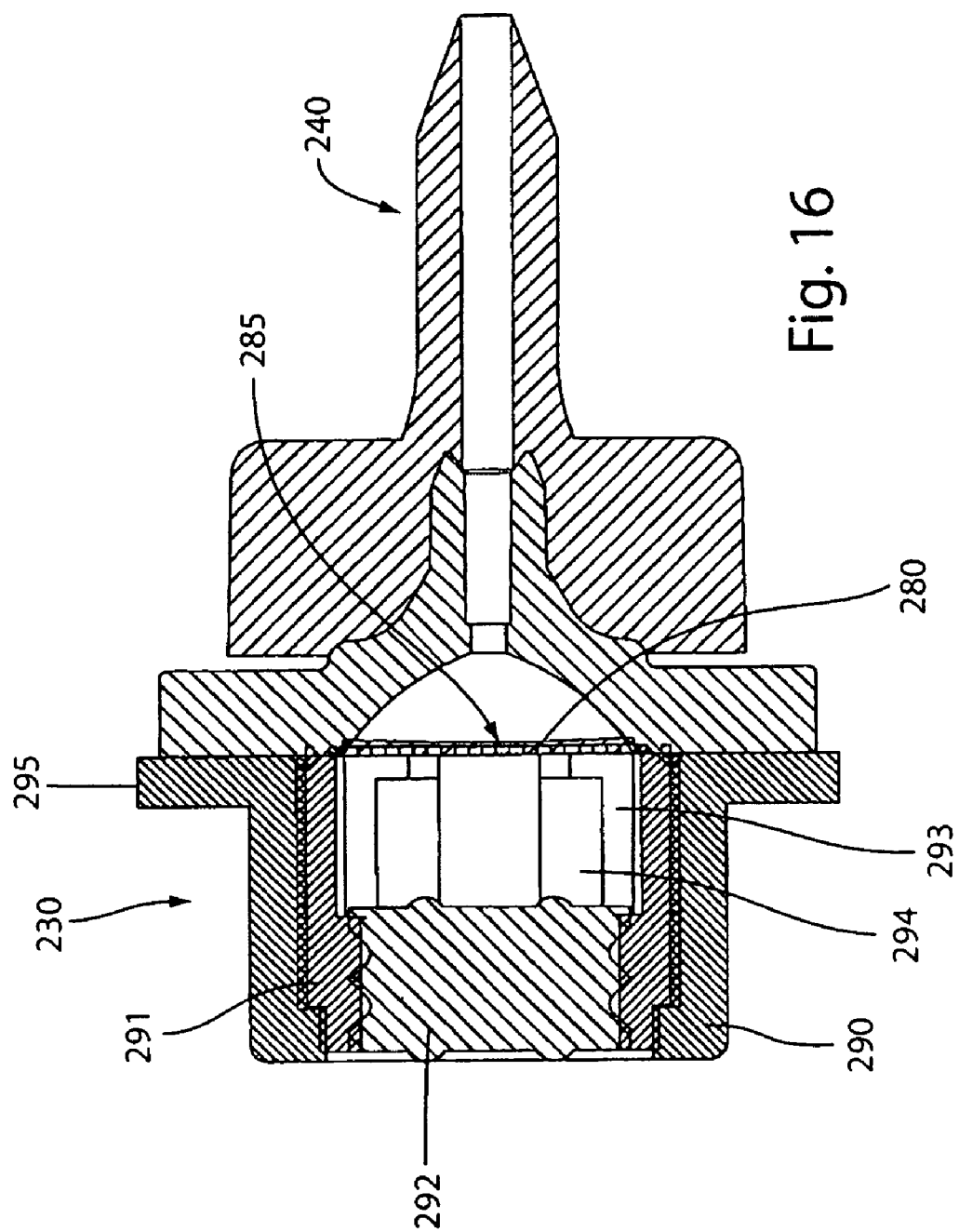
FIG. 16 is another longitudinal cross-sectional view of the seal structure and needle support of FIGS. 11-15.

FIG. 16 shows seal structure 230 and needle assembly 240 (without chamber 220 and clamp 242, for clarity). Seal structure 230 has outer seal 290, internal rigid member 291, and movable sealing plug 292. Outer seal 290 includes at least one side flange 295, and internal rigid member 291 has by-pass channel 293 such that movement of plug 292 to by-pass area 294 creates at least one flow path through by-pass channel 293. Positioned between seal structure 230 and needle assembly 240 and possibly attached to rigid member 291 is porous member 280, which contains therapeutic agent 285.

FIGS. 17 and 18 each show a method of assembling a thin or flat porous member, a seal structure, and a needle assembly. FIG. 17 shows porous member 380, which carries a therapeutic agent (not shown), secured to needle support 341 of a needle assembly 340. Seal structure 330 is then secured to needle assembly 340. FIG. 18 shows porous member 480, which carries therapeutic agent 485, secured to seal structure 430. The combined porous member and seal structure are then secured to the needle assembly. The porous member can be secured to the seal structure or needle support by any means known in the art. In certain preferred embodiments, the porous member is secured by sonic welding.

FIGS. 19 and 20 each show a method in which a therapeutic agent is applied to a thin or flat porous member. FIG. 19 shows a seal structure 530, a porous member 580, and a needle assembly 540. In this embodiment, therapeutic agent 585 is applied to the surface of porous member 580 that faces needle assembly 540 (i.e., the front surface). FIG. 20 shows a seal structure 630, a porous member 680, and a needle assembly 640. In this embodiment, the therapeutic agent is applied such that it fills the pores of porous member 680. Alternatively, the therapeutic agent can be applied to (1) the surface of porous member 580 that faces the seal structure (i.e., the rear surface), (2) both surfaces of the porous member, or (3) either or both surfaces and within the pores of the porous member.

The porous member is operative to carry a therapeutic agent and release the therapeutic agent into a liquid component flowing through the porous member. The porous member can be made out of any type of medically-appropriate material that can be made very thin or flat and have pores therethrough. The porous member can be fabricated from metallic, ceramic, or polymeric materials, or combinations thereof. Suitable metallic materials include alloys such as stainless steel.

Suitable ceramic materials include, but are not limited to, oxides, carbides, and nitrides of the transition elements such as titanium oxides, hafnium oxides, iridium oxides, chromium oxides, aluminum oxides, and zirconium oxides. Silicon based materials, such as silica, may also be used.

Suitable polymeric materials for forming the porous member include, but are not limited to, isobutylene-based polymers, polystyrene-based polymers, polyacrylates and polyacrylate derivatives, vinyl acetate-based polymers and its copolymers, polyurethane and its copolymers, silicone and its copolymers, ethylene vinyl-acetate, polyethylene terephtalate, thermoplastic elastomers, polyvinyl chloride, polyolefins, cellulosics, polyamides, polyesters, polysulfones, polytetrafluoroethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins.

Other polymers that are useful as materials for forming the porous member include, without limitation, dacron polyester, poly(ethylene terephthalate), polycarbonate, polymethylmethacrylate, polypropylene, polyalkylene oxalates, polyvinylchloride, polyurethanes, polysiloxanes, nylons, poly(dimethyl siloxane), polycyanoacrylates, polyphosphazenes, poly (amino acids), ethylene glycol I dimethacrylate, poly(methyl methacrylate), poly(2-hydroxyethyl methacrylate), polytetrafluoroethylene poly(HEMA), polyhydroxyalkanoates, polytetrafluorethylene, polycarbonate, poly(glycolide-lactide) co-polymer, polylactic acid, poly(γ-caprolactone), poly (γ-hydroxybutyrate), polydioxanone, poly(γ-ethyl glutamate), polyiminocarbonates, poly(ortho ester), polyanhydrides, alginate, dextran, chitin, cotton, polyglycolic acid, polyurethane, or derivatized versions thereof, i.e., polymers which have been modified to include, for example, attachment sites or cross-linking groups, e.g., RGD, in which the polymers retain their structural integrity while allowing for attachment of cells and molecules, such as proteins, nucleic acids, and the like.

The particular size and shape of the thin or flat porous member depends on the automatic injector in which it will be used. Generally, the porous member is the shape of a thin or flat disc or membrane as shown in FIGS. 17-20, which shows the porous member having a thin profile or minimal thickness (measured in the longitudinal direction of the interior chamber). Representative thicknesses for porous members of the invention range from about 0.005 inches (0.13 mm) to about 0.012 inches (0.30 mm) for polymeric materials and from about 0.010 inches (0.25 mm) to about 0.020 inches (0.51 mm) for metallic membranes. The diameter/width of a representative porous member (measured in the lateral direction of the interior chamber) is about 0.30 inches (7.62 mm), so the ratio of porous membrane diameter/width to thickness ranges from about 15:1 to 60:1. Thus, for all practical purposes, the thickness of the porous member, and its volume for that matter, can be considered negligible with respect to providing space in the longitudinal direction of and within a chamber in an automatic injector, wherein the term "negligible" as used herein is defined as being so small or unimportant as to warrant little or no attention.

Advantages of the thin or flat therapeutic-agent-carrying porous members of the invention include (1) requiring little if any additional space within an automatic injector; (2) greater versatility in placing and securing the porous member within the automatic injector than in known injectors having a dry compartment and/or using scaffolds, substrates, sponges, cell structures, and tubular networks; and (3) more rapid mixing of the liquid component with the therapeutic agent than in known injectors.

The porous member comprises a plurality of pores. The pores can be of different sizes or shapes. The pores can be interconnected or separate. The pores can also be distributed randomly or in a pattern. The size of the pores depends on the type of therapeutic agent used. The pores should be large enough to allow the liquid injection solution and the therapeutic agent to pass through. The average width or diameter of the pores ranges from about 0.02 microns to about 5 microns. Pores can be formed in the porous member by any method known in the art, such as sand blasting, drilling, laser etching, or chemical etching.

Preferred porous members include without limitation thin or flat metal discs with a plurality of pores therein, thin or flat filters such as ceramic or metallic filters, and thin or flat discs or membranes made of polymeric material.

Therapeutic agents used with porous members of the invention preferably include, but are not limited to, anti-asthmatics including beta-agonists such as salbutamol, levalbuterol, formoterol, fenoterol, salmeterol, bambuterol, brocaterol, clenbuterol, terbutalin, tuloburerol, epinephrin, isoprenalin, and hexoprenalin.

Other suitable therapeutic agents include, but are not limited to, anti-angiogenesis factors: antibodies; antigens: polysaccharides: growth factors; hormones including insulin, glucogen, parathyroid and pituitary hormones, calcitonin, vasopressin, renin, prolactin, growth hormones, thyroid stimulating hormone, corticotrophin, follicle stimulating hormone, luteinizing hormone, and chorionic gonadotropins; enzymes including soybean trypsin inhibitor, lysozyme, catalase, tumor angiogenesis factor, cartilage factor, transferases, hydrolases, lysases, isomerases, proteases, ligases and oxidoreductases such as esterases, phosphatases, glycosidases, and peptidases; enzyme inhibitors such as leupeptin, antipain, chymostatin and pepstatin; and drugs such as steroids, anticancer drugs, or antibiotics.

The amount of therapeutic agent disposed in and/or on the porous member depends on the therapeutic agent used. In many cases, the appropriate amount of therapeutic agent is less than or equal to about 25 mg.

The invention is also directed to a method of assembling an automatic injector, which includes filling a chamber with a liquid component and inserting a seal structure in the chamber. In some embodiments, inserting the seal structure into the chamber forms first and second compartments in the chamber. In other embodiments, a second compartment is not formed. The seal structure has a first position that seals the liquid component in the chamber (or first compartment) and a second position that creates a flow path through the seal structure from the chamber to a needle assembly (or from the first compartment to the second compartment and then to the needle assembly). The method further includes (1) applying a therapeutic agent to a thin or flat porous member, (2) securing the porous member at or after the end of the flow path, (3) mounting a needle assembly onto the chamber to dispense the therapeutic agent mixed with the liquid component, and (4) providing a housing to carry the injection device components.

As described above, the therapeutic agent can be applied to a surface of the porous member that faces the needle assembly and/or a surface that faces the seal structure. The therapeutic agent alternatively or additionally can be applied such that at least some, most, or all of the pores of the porous member are at least partially filled with the therapeutic agent. Moreover, as also described above, the porous member can be secured to the seal structure or the needle assembly. Note that the order of the above method steps can be varied. For example, applying the therapeutic agent and securing the porous member may occur before insertion of the seal structure or the filling of the chamber with the liquid component.

While the automatic injectors of the invention have been described herein with respect to the medical treatment of humans, they are not limited to such use. For example, automatic injectors of the invention may be alternatively used in connection with the treatment of animals and related scientific research thereof (for example, the injectors can be used to inject zoo animals, farm animals, or laboratory animals). Automatic injectors of the invention may also be alternatively used in connection with agriculture, horticulture, or forestry and related scientific research thereof (for example, the injector can be used to inject fruit, vegetables, trees, and/or other types of plant life).

The invention has been described in connection with the preferred embodiments. These embodiments, however, are merely examples, and the invention is not limited to them. Those skilled in the art understand that other variations and modifications may be easily made within the scope of the invention and that the invention is limited by only the following claims.

What is claimed is:

1. An automatic injector comprising:
   an interior chamber having an open end and containing a liquid component;
   a seal structure located in the interior chamber between the liquid component and the open end, the seal structure having a first state that seals the liquid component in the chamber and a second state that allows the liquid component to flow from the chamber through the seal structure;
   a needle assembly mounted to the open end of the interior chamber;
   a thin porous member located between the seal structure and the needle assembly, the porous member having a diameter/width measured in the lateral direction of the interior chamber that is no larger than a largest diameter/width of the interior chamber; and
   a therapeutic agent disposed on and/or in the porous member,
   wherein the thin porous member is separated from the liquid component by the seal structure.

2. The automatic injector of claim 1 wherein the porous member has a thickness ranging from 0.005 inches (0.13 mm) to about 0.020 inches (0.51 mm).

3. The automatic injector of claim 1 wherein the porous member has a thickness measured in the longitudinal direction of the interior chamber, the porous member having a ratio of diameter/width to thickness ranging from 15:1 to 60:1.

4. The automatic injector of claim 1 wherein the amount of therapeutic agent disposed on and/or in the porous member is less than or equal to 25 mg.

5. The automatic injector of claim 1 wherein the seal structure and the porous member are integrated into a single assembly.

6. The automatic injector of claim 1 wherein the porous member and the needle assembly are integrated into a single assembly.

7. The automatic injector of claim 1 wherein the porous member is sonically welded to either the seal structure or the needle assembly.

8. The automatic injector of claim 1 wherein the porous member comprises either a metallic, ceramic, or polymeric material, or a combination thereof.

9. The automatic injector of claim 1 wherein the porous member is a filter or polymer membrane.

10. The automatic injector of claim 1 wherein the porous member is a metal disc comprising a plurality of pores or holes.

11. The automatic injector of claim 1 wherein the porous member comprises a plurality of pores, the average pore width or diameter between about 0.02 microns to about 5 microns.

12. The automatic injector of claim 1 wherein the therapeutic agent is disposed within at least some of the pores of the porous member.

13. The automatic injector of claim 1 wherein the porous member has a first surface facing the needle assembly and a second surface facing the seal structure, the therapeutic agent disposed on at least one of the first and second surfaces.

14. The automatic injector of claim 1 wherein the therapeutic agent is epinephrine.

15. The automatic injector of claim 1 wherein the seal structure comprises:
   an outer seal;
   a rigid member disposed within the outer seal;
   an inner seal plug that has a first position with respect to the rigid member that seals the liquid component in the chamber and a second position with respect to the rigid member that allows the liquid component to flow through the seal structure; and at least one flow path through which the liquid component can pass when the seal structure is in the second position.

16. The automatic injector of claim 15 wherein the seal structure includes at least one by-pass channel that forms the at least one flow path and enables flow of the liquid component around the inner seal plug and through the seal structure when the inner seal plug is in the second position.

17. The automatic injector of claim 15 wherein the outer seal and the rigid member are configured to engage each other.

18. The automatic injector of claim 15 wherein the rigid member is formed from two rigid bodies that are annularly welded or bonded together.

19. The automatic injector of claim 18 wherein the porous member is between the two rigid bodies of the rigid member.

20. An automatic injector comprising:
an interior chamber having an open end and containing a liquid component, the interior chamber having a neck portion at the open end;
a seal structure positioned in the interior chamber at the open end in the neck portion, the seal structure convertible from a sealing condition, which seals the liquid component in the interior chamber, to a flow-through condition, which allows the liquid component to flow out of the interior chamber through a flow path;
a needle assembly mounted to the open end of the interior chamber;
a filter or membrane positioned between the seal structure and the needle assembly, the filter or membrane having a diameter/width measured in the lateral direction of the interior chamber that is no larger than a diameter/width of the neck portion; and
a therapeutic agent carried by the filter or membrane,
wherein the filter or membrane is separated from the liquid component by the seal structure.

21. The automatic injector of claim 20 wherein the seal structure and the filter or membrane are integrated into a single assembly.

22. The automatic injector of claim 20 wherein the needle assembly and the filter or membrane are integrated into a single assembly.

23. The automatic injector of claim 20 wherein the filter or membrane is sonically welded to either the seal structure or the needle assembly.

24. The automatic injector of claim 20 wherein the filter or membrane comprises either a metallic, ceramic, or polymeric material, or a combination thereof.

25. The automatic injector of claim 20 wherein the filter or membrane has a thickness measured in the longitudinal direction of the interior chamber, the filter or membrane having a ratio of diameter/width to thickness ranging from 15:1 to 60:1.

26. The automatic injector of claim 20 wherein the filter or membrane has a thickness ranging from about 0.005 inches (0.13 mm) to about 0.020 inches (0.51 mm).

27. The automatic injector of claim 20 wherein the filter or membrane has an area measured in the lateral direction of the interior chamber of about 0.07 square inches (45.6 mm$^2$).

28. The automatic injector of claim 20 wherein the filter or membrane is a metal disc comprising a plurality of pores or holes.

29. The automatic injector of claim 20 wherein the filter or membrane comprises a plurality of pores, the average pore width or diameter between about 0.02 microns to about 5 microns.

30. The automatic injector of claim 20 wherein the filter or membrane has a first surface facing the needle assembly and a second surface facing the sealing structure, the therapeutic agent disposed on at least one of the first and second surfaces.

31. The automatic injector of claim 20 wherein the therapeutic agent is disposed within at least some of the pores of the filter or membrane.

32. The automatic injector of claim 20 wherein the amount of therapeutic agent carried by the filter or membrane is less than or equal to 25 mg.

33. The automatic injector of claim 20 wherein the therapeutic agent is epinephrine.

34. The automatic injector of claim 20 wherein the seal structure comprises an outer seal and two rigid bodies annularly welded or bonded together, the two rigid bodies and the outer seal securingly engaged to each other, the filter or membrane secured between the two rigid bodies.

35. A method of assembling an automatic injector, comprising:
filling a chamber with a liquid component;
inserting a seal structure into the chamber, the seal structure convertible from a sealing condition, which seals the liquid component in the chamber, to a flow-through condition, which allows the liquid component to flow out of the chamber through a flow path;
applying a therapeutic agent to a flat porous member having a plurality of pores, the average pore width or diameter ranging between 0.02 microns and 0.9 microns, the porous member having a diameter/width measured in the lateral direction of the chamber that is no larger than a diameter/width of the chamber;
securing the porous member at or after the end of the flow path; and
mounting a needle assembly onto the chamber to dispense the therapeutic agent mixed with the liquid component,
wherein the flat porous member is separated from the liquid component by the seal structure.

36. The method of claim 35 wherein applying a therapeutic agent comprises applying a therapeutic agent to a flat porous member having a thickness ranging from about 0.005 inches (0.13 mm) to about 0.020 inches (0.51 mm).

37. The method of claim 35 wherein applying a therapeutic agent comprises applying a therapeutic agent to a surface of the porous member that faces the needle assembly.

38. The method of claim 35 wherein applying a therapeutic agent comprises applying a therapeutic agent to a surface of the porous member that faces the seal structure.

39. The method of claim 35 wherein applying a therapeutic agent comprises applying a therapeutic agent such that at least some of the pores of the porous member are at least partially filled with the therapeutic agent.

40. The method of claim 35 wherein securing the porous member comprises securing the porous member to the seal structure or to the needle assembly.

41. The method of claim 35 wherein applying the therapeutic agent and securing the porous member both occur before inserting the seal structure in the chamber.

42. An automatic injector comprising:
an interior chamber having an open end and containing a liquid component;
a seal structure positioned in the interior chamber, the seal structure having a first state that seals the liquid component in the chamber and a second state that allows the liquid component to flow from the chamber through the seal structure;
a needle assembly mounted to the open end of the interior chamber;
a thin porous member located between the seal structure and the needle assembly having a plurality of pores, the average pore width or diameter ranging between 0.02 microns and 0.9 microns, the porous member having a diameter/width measured in the lateral direction of the interior chamber that is no larger than a largest diameter/width of the interior chamber; and a therapeutic agent disposed on and/or in the porous member, wherein the thin porous member is separated from the liquid component by the seal structure.

43. The automatic injector of claim 42 wherein the porous member has a thickness ranging from 0.005 inches (0.13 mm) to about 0.020 inches (0.51 mm).

44. The automatic injector of claim 1 wherein the porous member has a thickness measured in the longitudinal direction of the interior chamber, the porous member having a ratio of diameter/width to thickness ranging from 15:1 to 60:1.

45. The automatic injector of claim 1 wherein the porous member is operative to have disposed thereon and/or therein a maximum of 25 mg of the therapeutic agent.

46. A method of assembling an automatic injector, comprising:

filling a chamber with a liquid component, the chamber having an open end and a neck portion at the open end;

inserting a seal structure in the neck portion of the chamber, the seal structure convertible from a sealing condition, which seals the liquid component in the chamber, to a flow-through condition, which allows the liquid component to flow out of the chamber through a flow path;

applying a therapeutic agent to a flat porous member, the porous member having a diameter/width measured in the lateral direction of the chamber that is no larger than a largest diameter/width of the chamber;

securing the porous member between the seal structure and the open end of the chamber; and mounting a needle assembly onto the chamber at the open end to dispense the therapeutic agent mixed with the liquid component, wherein the flat porous member is separated from the liquid component by the seal structure.

47. The method of claim 46 wherein applying a therapeutic agent comprises applying a therapeutic agent to a flat porous member having a thickness ranging from about 0.005 inches (0.13 mm) to about 0.020 inches (0.51 mm).

48. The method of claim 46 wherein applying a therapeutic agent comprises applying a therapeutic agent to a flat porous member having a plurality of pores, the average pore width or diameter ranging between 0.02 microns and 0.9 microns.

49. The method of claim 46 wherein securing the porous member comprises integrating the porous member and the seal structure into a single assembly.

50. The method of claim 46 wherein securing the porous member comprises integrating the porous member and the needle assembly into a single assembly.

51. The automatic injector of claim 1 wherein the porous member is attached to the seal structure.

* * * * *